United States Patent
Shino

(10) Patent No.: US 12,020,397 B2
(45) Date of Patent: Jun. 25, 2024

(54) LESION AREA DIVIDING DEVICE, MEDICAL IMAGE DIAGNOSTIC SYSTEM, LESION AREA DIVIDING METHOD, AND NON-TRANSITORY COMPUTER-READABLE MEDIUM STORING PROGRAM

(71) Applicant: NEC Corporation, Tokyo (JP)

(72) Inventor: Ryosaku Shino, Tokyo (JP)

(73) Assignee: NEC CORPORATION, Tokyo (JP)

( * ) Notice: Subject to any disclaimer, the term of this patent is extended or adjusted under 35 U.S.C. 154(b) by 405 days.

(21) Appl. No.: 17/430,062

(22) PCT Filed: Jan. 10, 2020

(86) PCT No.: PCT/JP2020/000712
§ 371 (c)(1),
(2) Date: Aug. 11, 2021

(87) PCT Pub. No.: WO2020/166247
PCT Pub. Date: Aug. 20, 2020

(65) Prior Publication Data
US 2022/0133214 A1      May 5, 2022

(30) Foreign Application Priority Data
Feb. 14, 2019   (JP) .................... 2019-024745

(51) Int. Cl.
*G06T 3/4007*      (2024.01)
*A61B 1/00*        (2006.01)
(Continued)

(52) U.S. Cl.
CPC ...... *G06T 3/4007* (2013.01); *A61B 1/000094* (2022.02); *A61B 5/444* (2013.01); (Continued)

(58) Field of Classification Search
CPC ... G06T 3/4007; G06T 3/4084; G06T 7/0012; G06T 3/00; G06T 2207/20021;
(Continued)

(56) References Cited

U.S. PATENT DOCUMENTS

2005/0190202 A1 * 9/2005 Suzuki .............. H04N 7/0122
                                                    348/E5.111
2006/0039630 A1    2/2006 Kotani
(Continued)

FOREIGN PATENT DOCUMENTS

EP      1475964 A1    11/2004
JP      H04195260 A    7/1992
(Continued)

OTHER PUBLICATIONS

International Search Report for PCT Application No. PCT/JP2020/000712, dated Mar. 24, 2020.
(Continued)

*Primary Examiner* — Ross Varndell
*Assistant Examiner* — Dustin Bilodeau

(57) ABSTRACT

A rectangle creating unit creates a rectangle circumscribing a lesion area in a medical image. A division-number-ratio calculating unit calculates a division-number ratio based on an image aspect ratio of an input image to be input to a device that identifies a lesion and on a rectangle aspect ratio between the length in the vertical direction of and the length in the horizontal direction of the rectangle. A multiplying-factor calculating unit calculates, based on the division-number ratio, a resizing multiplying-factor for each of the vertical direction and the horizontal direction of a rectangular image encircled by the rectangle and including the lesion area. A resizing unit resizes the rectangular image with the resizing multiplying-factor. A dividing unit divides the resized rectangular image into one or more images in
(Continued)

such a manner that the size of each divided image matches the size of the input image.

9 Claims, 10 Drawing Sheets

(51) Int. Cl.
*A61B 5/00* (2006.01)
*G06T 3/00* (2006.01)
*G06T 3/4084* (2024.01)
*G06T 7/00* (2017.01)
*G16H 50/20* (2018.01)

(52) U.S. Cl.
CPC .......... *G06T 3/4084* (2013.01); *G06T 7/0012* (2013.01); *G16H 50/20* (2018.01); *G06T 3/00* (2013.01); *G06T 2207/20021* (2013.01); *G06T 2207/30096* (2013.01)

(58) Field of Classification Search
CPC .... G06T 2207/30096; A61B 1/000094; A61B 5/444; A61B 1/00045; G16H 50/20; H04N 1/3875

See application file for complete search history.

(56) References Cited

U.S. PATENT DOCUMENTS

| | | | |
|---|---|---|---|
| 2007/0081721 A1* | 4/2007 | Xiao | .................... H04N 1/4074 |
| | | | 348/E5.073 |
| 2013/0294197 A1 | 11/2013 | Vallikkat Thachaparambil et al. | |
| 2016/0063721 A1 | 3/2016 | Nakano | |
| 2016/0350912 A1 | 12/2016 | Koide et al. | |
| 2019/0114738 A1* | 4/2019 | Sonoda | ............ A61B 1/000094 |

FOREIGN PATENT DOCUMENTS

| | | |
|---|---|---|
| JP | 2001223934 A | 8/2001 |
| JP | 2006094467 A | 4/2006 |
| JP | 2012090785 A | 5/2012 |
| JP | 2015-105841 A | 6/2015 |
| JP | 2015146970 A | 8/2015 |
| JP | 2016049454 A | 4/2016 |

OTHER PUBLICATIONS

Extended European Search Report for EP Application No. EP20755534.3 dated Mar. 10, 2022.

* cited by examiner

LESION AREA DIVIDING DEVICE, MEDICAL IMAGE DIAGNOSTIC SYSTEM, LESION AREA DIVIDING METHOD, AND NON-TRANSITORY COMPUTER-READABLE MEDIUM STORING PROGRAM

This application is a National Stage Entry of PCT/JP2020/000712 filed on Jan. 10, 2020, which claims priority from Japanese Patent Application 2019-024745 filed on Feb. 14, 2019, the contents of all of which are incorporated herein by reference, in their entirety.

TECHNICAL FIELD

The present invention relates to a lesion area dividing device, a medical image diagnostic system, a lesion area dividing method, and a non-transitory computer-readable medium storing a program.

BACKGROUND ART

Lesions are diagnosed using medical images. In connection with this technique, Patent Literature 1 discloses an endoscopic image diagnosis support system that identifies a pathologic type in an identification target region in an endoscopic image. The endoscopic image diagnosis support system according to Patent Literature 1 performs feature value matching between an image in the identification target region and each subdivided region of the identification target region and learning images to compute identification probabilities of the pathologic types in the identification target region and the subdivided regions.

In addition, Patent Literature 2 discloses an endoscopic device that freely sets a region desired to be enlarged in a normal observation image depending on the observation situation. The endoscopic device according to Patent Literature 2 determines, as the enlargement ratio for an entire enlarged display area, the enlargement ratio of one of the length and width of an input specification area specified by an operator's input operation to set an enlarged display area. In addition, Patent Literature 3 discloses an image filing system capable of filing high-quality image information. The image filing system according to Patent Literature 3 divides an input signal into a plurality of image signals to transmit an image recording/reproducing device and combines the divided image signals to be the original image signal.

CITATION LIST

Patent Literature

Patent Literature 1: Japanese Unexamined Patent Application Publication No. 2015-146970
Patent Literature 2: Japanese Unexamined Patent Application Publication No. 2012-090785
Patent Literature 3: Japanese Unexamined Patent Application Publication No. H4-195260

SUMMARY OF INVENTION

Technical Problem

In the technique disclosed in Patent Literature 1, a scan window is gradually subdivided to identify the pathologic type of an affected part having not a rectangular shape but a complicated shape. Thus, the sizes and shapes of the subdivided scan windows can cause deterioration in the accuracy of lesion diagnosis. Furthermore, with the techniques according to Patent Literature 2 and Patent Literature 3, it is difficult to prevent deterioration in the accuracy of lesion diagnosis.

In order to solve such a problem, a purpose of the present disclosure is to provide a lesion area dividing device, a medical image diagnostic system, a lesion area dividing method, and a program that are capable of preventing deterioration in the accuracy of lesion diagnosis regardless of the shape of a lesion area in a medical image.

Solution to Problem

A lesion area dividing device according to the present disclosure includes a rectangle creating means for creating a rectangle circumscribing a lesion area in a medical image, a division-number-ratio calculating means for calculating, based on an image aspect ratio of an input image to be input to a device that identifies a lesion and on a rectangle aspect ratio between a length in a vertical direction and a length in a horizontal direction of the rectangle, a division-number ratio of the number of divisions in a vertical direction to the number of divisions in a horizontal direction when the lesion area is divided, a multiplying-factor calculating means for calculating, based on the division-number ratio, a resizing multiplying-factor for each of a vertical direction and a horizontal direction of a rectangular image encircled by the rectangle and including the lesion area, a resizing means for resizing the rectangular image with the resizing multiplying-factor, and a dividing means for dividing the resized rectangular image into one or more images in such a manner that a size of each divided image matches a size of the input image.

In addition, a medical image diagnostic system according to the present disclosure includes a lesion area dividing device that divides a lesion area in a medical image, and a lesion identifying device that identifies a lesion using the divided lesion area, in which the lesion area dividing device includes a rectangle creating means for creating a rectangle circumscribing the lesion area, a division-number-ratio calculating means for calculating, based on an image aspect ratio of an input image to be input to the lesion identifying device and on a rectangle aspect ratio between a length in a vertical direction and a length in a horizontal direction of the rectangle, a division-number ratio of the number of divisions in a vertical direction to the number of divisions in a horizontal direction when the lesion area is divided, a multiplying-factor calculating means for calculating, based on the division-number ratio, a resizing multiplying-factor for each of a vertical direction and a horizontal direction of a rectangular image encircled by the rectangle and including the lesion area, a resizing means for resizing the rectangular image with the resizing multiplying-factor, and a dividing means for dividing the resized rectangular image into one or more images in such a manner that a size of each divided image matches a size of the input image, and the lesion identifying device identifies a lesion using each divided image.

In addition, a lesion area dividing method according to the present disclosure includes creating a rectangle circumscribing a lesion area in a medical image, calculating, based on an image aspect ratio of an input image to be input to a device that identifies a lesion and on a rectangle aspect ratio between a length in a vertical direction and a length in a horizontal direction of the rectangle, a division-number ratio of the number of divisions in a vertical direction to the number of divisions in a horizontal direction when the lesion area is divided, calculating, based on the division-number ratio, a resizing multiplying-factor for each of a vertical direction and a horizontal direction of a rectangular image encircled by the rectangle and including the lesion area, resizing the rectangular image with the resizing multiplying-factor, and dividing the resized rectangular image into one or more images in such a manner that a size of each divided image matches a size of the input image.

In addition, a program according to the present disclosure causes a computer to execute a step of creating a rectangle circumscribing a lesion area in a medical image, a step of calculating, based on an image aspect ratio of an input image to be input to a device that identifies a lesion and on a rectangle aspect ratio between a length in a vertical direction and a length in a horizontal direction of the rectangle, a division-number ratio of the number of divisions in a vertical direction to the number of divisions in a horizontal direction when the lesion area is divided, a step of calculating, based on the division-number ratio, a resizing multiplying-factor for each of a vertical direction and a horizontal direction of a rectangular image encircled by the rectangle and including the lesion area, a step of resizing the rectangular image with the resizing multiplying-factor, and a step of dividing the resized rectangular image into one or more images in such a manner that a size of each divided image matches a size of the input image.

Advantageous Effects of Invention

According to the present disclosure, it is possible to provide a lesion area dividing device, a medical image diagnostic system, a lesion area dividing method, and a program that are capable of preventing deterioration in the accuracy of lesion diagnosis regardless of the shape of a lesion area in a medical image.

DESCRIPTION OF EMBODIMENTS (Outline of an Example Embodiment According to the Present Disclosure)

Figure 1:
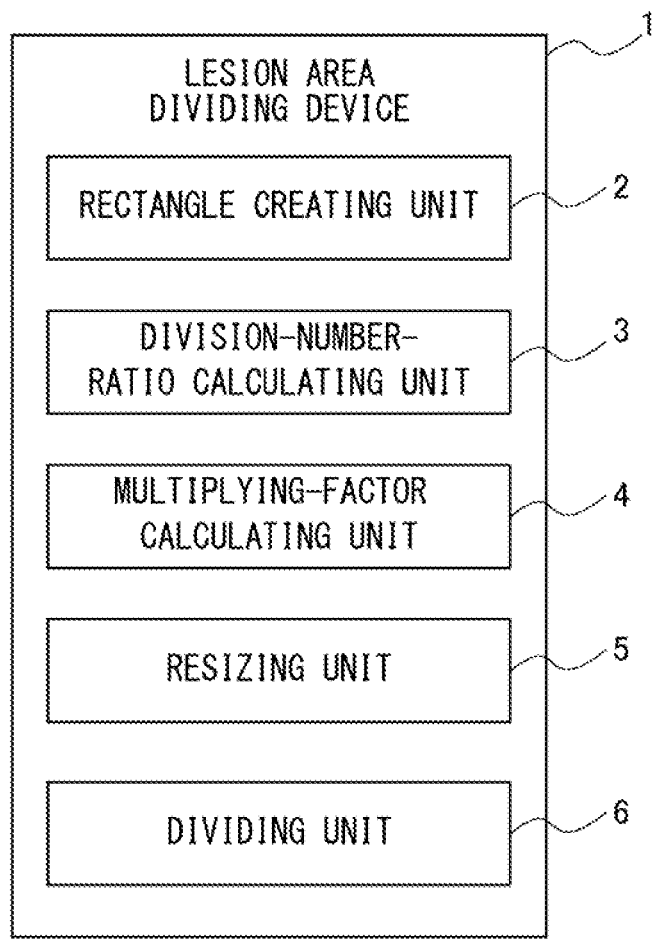
FIG. 1 is a diagram showing an outline of a lesion area dividing device according to an example embodiment of the present disclosure.

Before an example embodiment of the present disclosure is described, an outline of the example embodiment according to the present disclosure is described. FIG. 1 shows an outline of a lesion area dividing device 1 according to the example embodiment of the present disclosure. The lesion area dividing device 1 has a function as, for example, a computer.

The lesion area dividing device 1 includes a rectangle creating unit 2, a division-number-ratio calculating unit 3, a multiplying-factor calculating unit 4, a resizing unit 5, and a dividing unit 6. The rectangle creating unit 2 has a function as a rectangle creating means. The division-number-ratio calculating unit 3 has a function as a division-number-ratio calculating means. The multiplying-factor calculating unit 4 has a function as a multiplying-factor calculating means. The resizing unit 5 has a function as a resizing means. The dividing unit 6 has a function as a dividing means.

The rectangle creating unit 2 creates a rectangle circumscribing a lesion area in a medical image. The division-number-ratio calculating unit 3 calculates a division-number ratio based on an image aspect ratio of an input image to be input to a device that identifies a lesion and on a rectangle aspect ratio between the length in the vertical direction and the length in the horizontal direction of the rectangle. Here, the division-number ratio is a ratio of the number of divisions in the vertical direction to the number of divisions in the horizontal direction when the lesion area is divided. The multiplying-factor calculating unit 4 calculates, based on the division-number ratio, the resizing multiplying-factor for each of the vertical direction and the horizontal direction of a rectangular image encircled by the rectangle and including the lesion area. The resizing unit 5 resizes the rectangular image with the resizing multiplying-factor (changes the size of the rectangular image). The dividing unit 6 divides the resized rectangular image into one or more images in such a manner that the size of each divided image matches the size of the input image.

In lesion diagnosis using medical images, the size of an image (an input image) to be input to a device used for diagnosis is mainly fixed. Thus, a medical image can be divided and enlarged or reduced to match the size of the input image. In this case, if a medical image is too subdivided, the subdivided image needs to be greatly enlarged to match the size of the input image. This can cause deterioration in the accuracy of diagnosis. In addition, the lesion area in a medical image is varied in shape and is vertically long or horizontally long. In this case, if a vertically-long lesion area is too enlarged in the horizontal direction to match the aspect ratio of the input image, the shape of the lesion area changes greatly. This can cause deterioration in the accuracy of diagnosis.

In contrast, the lesion area dividing device 1 according to the present example embodiment is configured to divide the rectangular image in consideration of the image aspect ratio of the input image to be input to the device that identifies a lesion and the rectangle aspect ratio of the rectangular image including the lesion area as described above. For this reason, it is possible to minimize the change in the rectangle aspect ratio and to divide the rectangular image to match the size of the input image. Thus, the lesion area dividing device 1 according to the present example embodiment is capable of preventing deterioration in the accuracy of lesion diagnosis regardless of the shape of the lesion area in a medical image.

Note that, with a medical image diagnostic system including the lesion area dividing device 1 and a lesion identifying device configured to identify a lesion, it is possible to prevent deterioration in the accuracy of lesion diagnosis regardless of the shape of the lesion area in a medical image. In addition, with a lesion area dividing method to be performed by the lesion area dividing device 1, it is possible to prevent deterioration in the accuracy of lesion diagnosis regardless of the shape of the lesion area in a medical image. Furthermore, with a program capable of executing the lesion area dividing method, it is possible to prevent deterioration in the accuracy of lesion diagnosis regardless of the shape of the lesion area in a medical image.

First Example Embodiment

Hereinafter, an example embodiment is described with reference to the drawings. For the sake of clarity, the following description and the drawings are appropriately omitted and simplified. In addition, the same elements in the drawings are denoted by the same reference signs, and the duplicate description is omitted as necessary.

Figure 2:
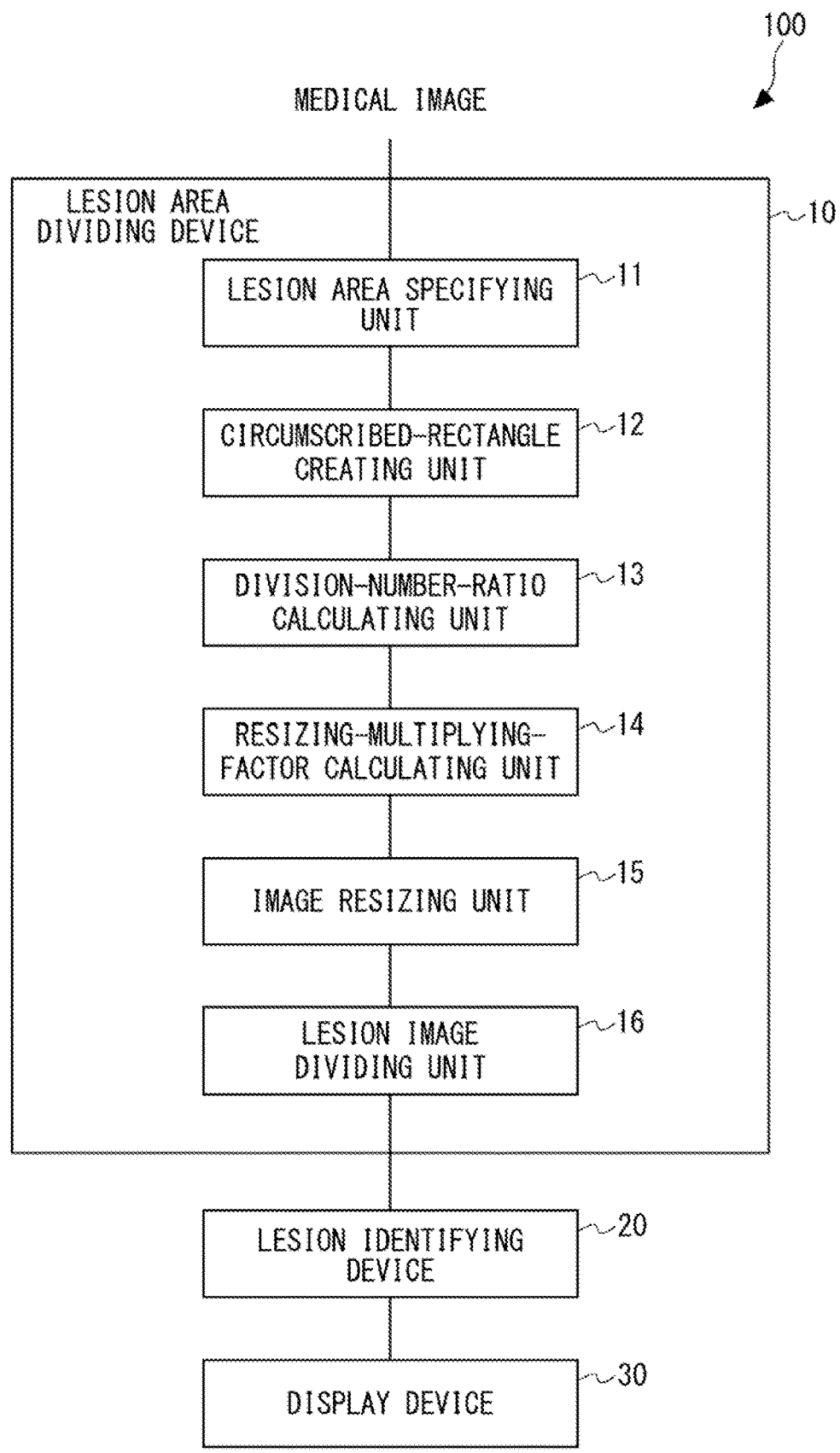
FIG. 2 is a block diagram showing a configuration of a medical image diagnostic system according to a first example embodiment.
Figure 3:
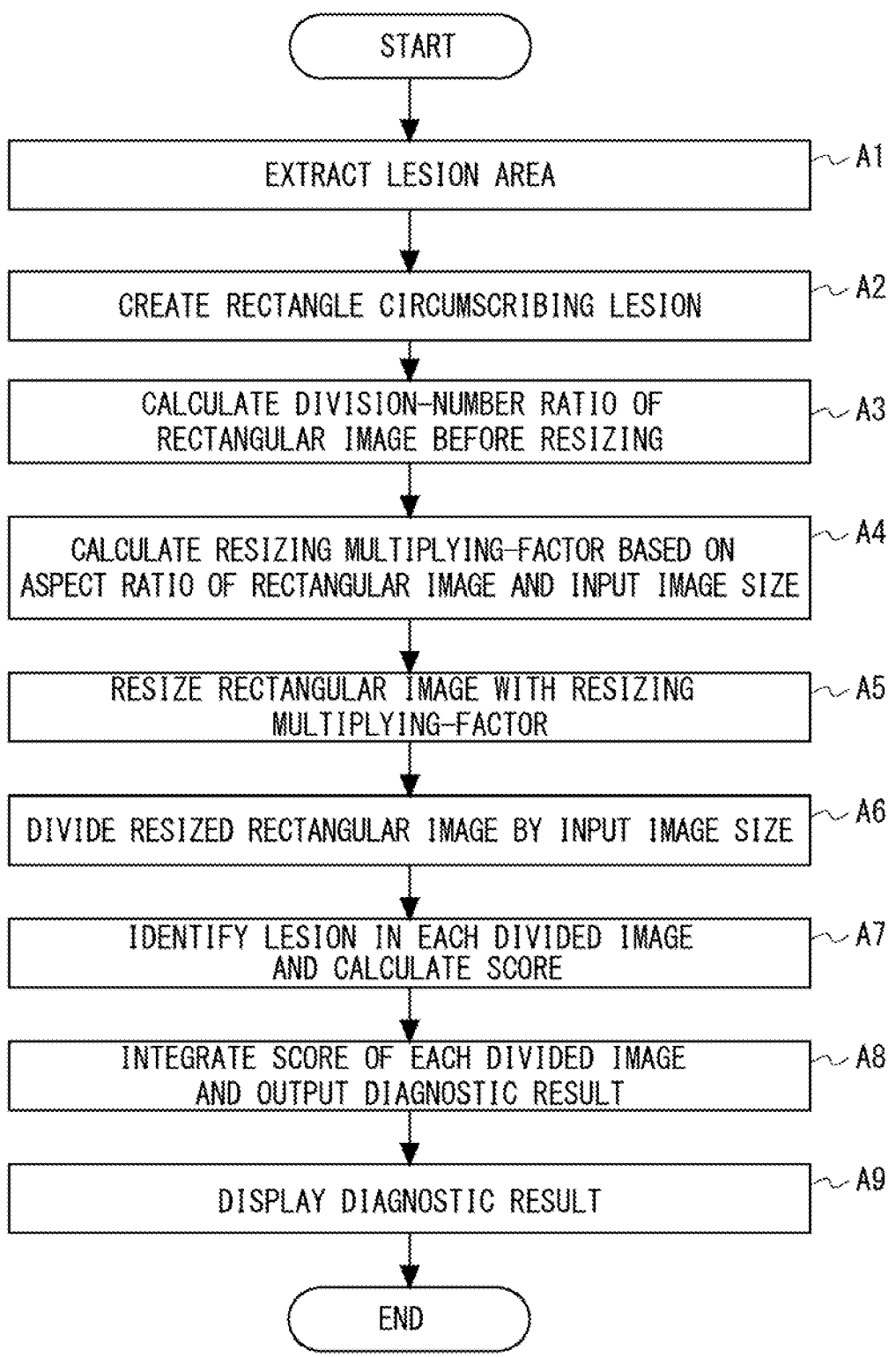
FIG. 3 is a flowchart showing a medical image diagnostic method performed by the medical image diagnostic system according to the first example embodiment.

FIG. 2 is a block diagram showing a configuration of a medical image diagnostic system 100 according to the first example embodiment. FIG. 3 is a flowchart showing a medical image diagnostic method to be performed by the medical image diagnostic system 100 according to the first example embodiment. The medical image diagnostic system 100 includes a lesion area dividing device 10, a lesion identifying device 20, and a display device 30. The lesion area dividing device 10 is a computer. The lesion area dividing device 10 is implemented by hardware, such as a processing unit, a random access memory, a hard disk drive, a mother board, a power source, and a universal serial bus (USB) terminal. The processing unit is implemented by, for example, a central processing unit (CPU), a field programmable gate array (FPGA), a graphics processing unit (GPU) or the like. The lesion identifying device 20 is a computer implemented by hardware similar to the lesion area dividing device 10. The display device 30 is a display implemented by hardware, such as a monitor, a speaker, and an interface. The monitor is implemented by, for example, a cathode ray tube (CRT) or a liquid crystal display (LCD). The interface is implemented by, for example, a high-definition multimedia interface (HDMI) (registered trademark) terminal, a digital visual interface (DVI) terminal, a HDMI cable, and a DVI cable.

The lesion area dividing device 10 includes a lesion area specifying unit 11, a circumscribed-rectangle creating unit 12, a division-number-ratio calculating unit 13, a resizing-multiplying-factor calculating unit 14, an image resizing unit 15, and a lesion image dividing unit 16. The circumscribed-rectangle creating unit 12 corresponds to the rectangle creating unit 2 in FIG. 1. The division-number-ratio calculating unit 13 corresponds to the division-number-ratio calculating unit 3 in FIG. 1. The resizing-multiplying-factor calculating unit 14 corresponds to the multiplying-factor calculating unit 4 in FIG. 1. The image resizing unit 15 corresponds to the resizing unit 5 in FIG. 1. The lesion image dividing unit 16 corresponds to the dividing unit 6 in FIG. 1.

The lesion area specifying unit 11 has a function as a lesion area specifying means. The lesion area specifying unit 11 specifies a lesion area in a medical image, such as an endoscopic image. The circumscribed-rectangle creating unit 12 has a function as a circumscribed-rectangle creating means. The circumscribed-rectangle creating unit 12 creates, from information about the lesion area in the medical image, a rectangle circumscribing the lesion. The division-number-ratio calculating unit 13 has a function as a division-number-ratio calculating means. The division-number-ratio calculating unit 13 calculates, from an input image size of the lesion identifying device 20 and the size of the rectangle circumscribing the lesion, the number of divisions in the vertical direction and the number of divisions in the horizontal direction of the rectangle to calculate a division-number ratio, which is the ratio between the number of divisions in the vertical direction and the number of divisions in the horizontal direction of the image. Here, the input image size is the size of an image to be input to the lesion identifying device 20. In addition, the image to be input to the lesion identifying device 20 is referred to as an input image.

The resizing-multiplying-factor calculating unit 14 has a function as a resizing-multiplying-factor calculating means. The resizing-multiplying-factor calculating unit 14 refers to the division-number ratio to calculate a multiplying-factor (resizing multiplying-factor) for resizing a rectangular area (rectangular image) encircled by the rectangle circumscribing the lesion. The image resizing unit 15 has a function as an image resizing means. The image resizing unit 15 resizes the rectangular image based on the resizing multiplying-factor (changes the size of the rectangular image). The lesion image dividing unit 16 has a function as a lesion image dividing means. The lesion image dividing unit 16 divides the resized rectangular image by the input image size.

The medical image diagnostic system 100 receives a medical image, identifies the lesion in the image, and visualizes the result on the display device 30. Here, the medical image is described as an endoscopic image in the present example embodiment, but the medical image is not limited to an endoscopic image. For example, the medical image may be an X-ray image, a computed tomography (CT) image, or a magnetic resonance imaging (MRI) image.

The lesion area dividing device 10 receives the medical image, extracts the lesion area in the image, crops (extracts) a rectangular area circumscribing the lesion area, resizes the cropped rectangular area (rectangular image) to match the input image size of the lesion identifying device 20, and divides it. The lesion identifying device 20 receives, as an input image, an image around the lesion area formed to have a fixed size (input image size), identifies the pathologic type, the invasion depth, the malignancy, and the like of the lesion in the image, and outputs a data string for the identification result. The display device 30 receives the data string for the identification result and presents the identification result to the user with characters, a still image, a moving image, sounds, or the like.

The lesion area specifying unit 11 receives the medical image, extracts the lesion area in the medical image, and outputs a data string for position information about the extracted lesion area. The circumscribed-rectangle creating unit 12 accepts the data string for the position information about the lesion area in the image and outputs a data string for position information about the rectangle circumscribing the lesion area. The division-number-ratio calculating unit 13 accepts the data string for the position information about the rectangle circumscribing the lesion area, calculates a ratio (rectangle aspect ratio) between the vertical and horizontal lengths of the rectangle circumscribing the lesion area, and outputs numerical data of the rectangle aspect ratio. The resizing-multiplying-factor calculating unit 14 accepts the medical image, the data string for the position information about the rectangle circumscribing the lesion area in the image, and the numerical data of the rectangle aspect ratio and crops (extracts) the medical image as the rectangle circumscribing the lesion area. Then, the resizing-multiplying-factor calculating unit 14 determines a resizing multiplying-factor using the input image size of the lesion identifying device 20 and the numerical value of the rectangle aspect ratio. The image resizing unit 15 resizes, with the determined resizing multiplying-factor, the rectangular image obtained by being cropped. The lesion image dividing unit 16 accepts the rectangular image output from the image resizing unit 15 and divides the input image by the input image size of the lesion identifying device 20.

[Description of Operation]

Next, with reference to the flowchart in FIG. 3, the whole operation in the present example embodiment is detailedly described. First, the lesion area specifying unit 11 extracts a lesion area from a medical image (step A1). Specifically, the lesion area specifying unit 11 scans all the pixels of the input medical image and calculates the score indicating the lesion-likeness in each pixel. This score is represented by, a value from 0 to 1 and indicates that the lesion-likeness is increased as the value is higher. Then, the lesion area specifying unit 11 specifies a pixel having a score equal to or higher than a specified threshold as a pixel including the imaged lesion. Then, the lesion area specifying unit 11 creates an output data string having the same size as the image size and inputs "1" to the position corresponding to the pixel including the imaged lesion and "0" to the position corresponding to the pixel including no imaged lesion. Thereafter, the lesion area specifying unit 11 outputs the data string containing the information about the lesion area to the circumscribed-rectangle creating unit 12 and output the medical image to the image resizing unit 15. Note that, the process for specifying a pixel including the imaged lesion can be performed by, for example, machine learning or the like.

Next, the circumscribed-rectangle creating unit 12 creates a rectangle circumscribing the lesion (step A2). Specifically, the circumscribed-rectangle creating unit 12 scans a data string containing information about the lesion area to calculate the minimum value and the maximum value for each of the X-coordinate and the Y-coordinate of the pixel including the imaged lesion. Then, the circumscribed-rectangle creating unit 12 outputs a data string indicating the calculation result to the division-number-ratio calculating unit 13 and the image resizing unit 15.

The division-number-ratio calculating unit 13 calculates the division-number ratio of the rectangular image before resizing (step A3). Specifically, the division-number-ratio calculating unit 13 calculates, as a reference value of the division-number ratio before resizing, a ratio (division-number ratio) between the number of divisions in the vertical direction and the number of divisions in the horizontal direction of the rectangular image including the lesion area in order not to greatly change the rectangle aspect ratio of the rectangular image after resizing. As a concrete algorithm, the division-number-ratio calculating unit 13 calculates a length $l_x$ of the rectangle circumscribing the lesion area (rectangular image) in the horizontal direction from the difference between the maximum value and the minimum value for the X-coordinate of the lesion area. Similarly, the division-number-ratio calculating unit 13 calculates a length $l_y$ of the rectangle circumscribing the lesion area (rectangular image) in the vertical direction from the difference between the maximum value and the minimum value for the Y-coordinate of the lesion area. Note that, the X direction corresponds to the horizontal direction of the rectangular image (lesion area), and the Y direction corresponds to the vertical direction of the rectangular image (lesion area).

The division-number-ratio calculating unit 13 further calculates, using the input image size, a ratio $R_{original}$ between the number of divisions in the X direction and the number of divisions in the Y direction when the lesion area before resizing is divided by the input image size of the lesion identifying device 20. Here, regarding the input image size, the size in the X direction is represented by $w_{in}$, and the size in the Y direction is represented by $h_{in}$.

$R_{original}$ is calculated using the following Expression 1. Note that, $R_{original}$ represents the ratio of the number of divisions in the vertical direction of the rectangular image before resizing to the number of divisions in the horizontal direction. The division-number-ratio calculating unit 13 calculates $R_{original}$ of the rectangular image before resizing and then outputs the value of $R_{original}$ to the image resizing unit 15.

[Expression 1]

$$R_{original} = \frac{l_y w_{in}}{l_x h_{in}} \quad (1)$$

Note that, since the rectangle aspect ratio before resizing is $l_y/l_x$ and the image aspect ratio is $h_{in}/w_{in}$, $R_{original}$ can be said as the ratio of the rectangle aspect ratio to the image aspect ratio. Thus, the division-number-ratio calculating unit 13 calculates the division-number ratio based on the image aspect ratio and the rectangle aspect ratio.

Figure 4:
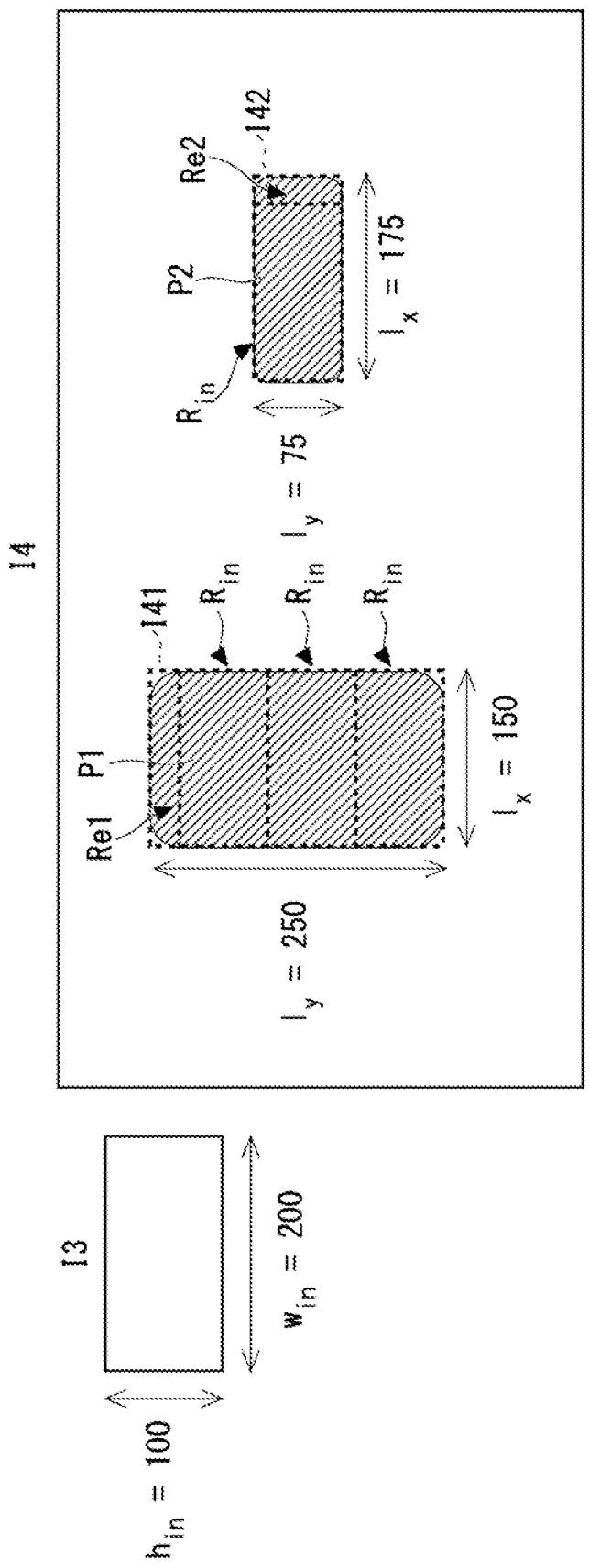
FIG. 4 is a diagram for explaining a process of a division-number-ratio calculating unit according to the first example embodiment.

FIG. 4 is a diagram for explaining a process of the division-number-ratio calculating unit 13 according to the first example embodiment. FIG. 4 exemplifies an input image I3 to be input to the lesion identifying device 20 and a rectangular image I4. The rectangular image I4 includes a rectangular image I41 including a lesion P1, and a rectangular image I42 including a lesion P2. The input image size of the input image I3 is 100×200 pixels ($h_{in}$=100, $w_{in}$=200). In addition, the size of the rectangular image I41 is 250×150 pixels ($l_y$=250, $l_x$=150), and the size of the rectangular image I42 is 75×175 pixels ($l_y$=75, $l_x$=175).

Note that, in the rectangular image I4 shown in FIG. 4, each rectangle $R_{in}$ indicated by a broken line is a rectangle formed to have the aspect ratio (image aspect ratio) of the input image I3. In this case, the rectangular image I41 including the lesion P1 includes three rectangles $R_{in}$ (75×150 pixels) each having the image aspect ratio and a residual portion Re1 (25×150 pixels). The rectangular image I42 including the lesion P2 includes one rectangle $R_{in}$ (75×150 pixels) having the image aspect ratio and a residual portion Re2 (75×25 pixels). In this manner, if the rectangular image before resizing is divided by the rectangle having the image aspect ratio, the residual portions are generated.

When accepting the rectangular image I41, the division-number-ratio calculating unit 13 calculates $R_{original}$ as 10/3 using Expression 1. Thus, the ratio of the number of divisions in the vertical direction of the rectangular image I41 before resizing to the number of divisions in the horizontal direction is 10/3. This means that the rectangular image I41 is divided into three in the horizontal direction and into ten in the vertical direction if the rectangular image I41 is divided to match the aspect ratio (image aspect ratio) of the input image without resizing as the process in A5 described later.

Alternatively, when accepting the rectangular image I42, the division-number-ratio calculating unit 13 calculates $R_{original}$ as 6/7 using Expression 1. Thus, the ratio of the number of divisions in the vertical direction of the rectangular image I42 before resizing to the number of divisions in the horizontal direction is 6/7. This means that the rectangular image I42 is divided into seven in the horizontal direction and into six in the vertical direction if the rectangular image I42 is divided to match the image aspect ratio without resizing as the process in A5 described later.

The resizing-multiplying-factor calculating unit 14 calculates the resizing multiplying-factor based on the rectangle aspect ratio of the rectangular image and the input image size (step A4). Specifically, the resizing-multiplying-factor calculating unit 14 crops (extracts), using the minimum value and the maximum value for each of the X-coordinate and the Y-coordinate of the pixel including the imaged lesion, the rectangular image including the imaged lesion in the medical image. The resizing-multiplying-factor calculating unit calculates, using the division-number ratio $R_{original}$ of the rectangular area before resizing and an upper limit value $d_{max}$ of the number of divisions, a division-number ratio $R_{adjusted}$ after resizing. Here, $R_{adjusted}$ represents the ratio of the number of divisions in the vertical direction of the rectangular image after resizing to the number of divisions in the horizontal direction. In addition, the upper limit value $d_{max}$ is the upper limit value of the number of divisions in the vertical direction and the horizontal direction and can be preset by the user. Accordingly, as described later, it is possible to obtain the number of divisions after resizing with which the change in the aspect ratio (rectangle aspect ratio) of the rectangular image obtained by being cropped is minimized and the number of divisions in each of the vertical direction and the horizontal direction does not exceed the upper limit value $d_{max}$.

Here, a method for calculating $R_{adjusted}$ is any one of the following three methods depending on the magnitude of the value of $R_{original}$. That is, the resizing-multiplying-factor calculating unit 14 calculates the division-number ratio of the rectangular image after resizing by a calculation method which differs depending on the magnitude of the division-number ratio $R_{original}$ with respect to predetermined thresholds Th1 (a first threshold) and Th2 (a second threshold). That is, the method for calculating $R_{adjusted}$ differs in the case of $R_{original}$<Th1, Th1≤$R_{original}$<Th2, or Th2≤$R_{original}$. These correspond to, regarding the rectangular image before resizing, the case where "the number of divisions in the horizontal direction is sufficiently greater than the number of divisions in the vertical direction", the case where "the number of divisions in the vertical direction is substantially equal to the number of divisions in the horizontal direction", and the case where "the number of divisions in the vertical direction is sufficiently greater than the number of divisions in the horizontal direction".

Note that, the thresholds Th1 and Th2 are set using the upper limit value $d_{max}$. In addition, Th1<1 and Th2>1 hold. With these, the resizing-multiplying-factor calculating unit 14 calculates the division-number ratio of the rectangular image after resizing in such a manner that the number of divisions in the vertical direction and the number of divisions in the horizontal direction of the rectangular image after resizing do not exceed the upper limit value $d_{max}$ of the number of divisions.

<In the Case where the Number of Divisions in the Horizontal Direction is Sufficiently Greater than the Number of Divisions in the Vertical Direction>

If $R_{original}$ satisfies the following Expression 2, the number of divisions in the horizontal direction of the rectangular image before resizing can be said to be sufficiently greater than the number of divisions in the vertical direction. Here, the right side of Expression 2 corresponds to the threshold Th1.

[Expression 2]
$$R_{original} < \frac{2d_{max} - 1}{2d_{max}} \qquad (2)$$

In this case, by setting the number of divisions in the horizontal direction of the rectangular image after resizing as the upper limit value $d_{max}$, $R_{adjusted}$ is calculated using the following Expression 3.

[Expression 3]
$$R_{adjusted} = \frac{d}{d_{max}} \qquad (3)$$

Here, d is the number of divisions in the short-side direction (vertical direction) and is a natural number satisfying the following Expression 4. Accordingly, d is the natural number closest to $d^{max}R_{original}$. Here, $d_{max}R_{original}$≥½ is set. That is, $R_{original}$ is small if the rectangular image is excessively long in the horizontal direction, and $d_{max}$ may be set to be large. In addition, from Expression 2, d satisfying Expression 4 is less than $d_{max}$.

[Expression 4]
$$d_{max}R_{original} - \frac{1}{2} < d \leq d_{max}R_{original} + \frac{1}{20} \qquad (4)$$

<In the Case where the Number of Divisions in the Vertical Direction is Substantially Equal to the Number of Divisions in the Horizontal Direction>

If $R_{original}$ satisfies the following Expression 5, the number of divisions in the vertical direction of the rectangular image before resizing can be said to be substantially equal to the number of divisions in the horizontal direction. Here, the rightmost side of Expression 5 corresponds to the threshold Th2.

[Expression 5]
$$\frac{2d_{max} - 1}{2d_{max}} \leq R_{original} < \frac{2d_{max}}{2d_{max} - 1} \qquad (5)$$

In this case, by setting the number of divisions in the vertical direction of the rectangular image after resizing to be equal to the number of divisions in the horizontal direction, $R_{adjusted}$ is calculated using the following Expression 6.

[Expression 6]
$$R_{adjusted} = 1 \qquad (6)$$

<In the Case where the Number of Divisions in the Vertical Direction is Sufficiently Greater than the Number of Divisions in the Horizontal Direction>

If $R_{original}$ satisfies the following Expression 7, the number of divisions in the vertical direction can be said to be sufficiently greater than the number of divisions in the horizontal direction.

[Expression 7]

$$\frac{2d_{max}}{2d_{max}-1} \leq R_{original} \tag{7}$$

In this case, by setting the number of divisions in the vertical direction of the rectangular image after resizing as the upper limit value $d_{max}$, $R_{adjusted}$ is calculated using the following Expression 8.

[Expression 8]

$$R_{adjusted} = \frac{d_{max}}{d} \tag{8}$$

Here, the number of divisions d in the short-side direction (horizontal direction) is a natural number satisfying the following Expression 9.

Accordingly, d is the natural number closest to $d_{max}/R_{original}$. Here, $d_{max}/R_{original} > \frac{1}{2}$ is set. That is, $R_{original}$ is large if the rectangular image is excessively long in the vertical direction, and $d_{max}$ may be set to be large. In addition, from Expression 7, d satisfying Expression 9 is less than $d_{max}$.

[Expression 9]

$$\frac{d_{max}}{R_{original}} - \frac{1}{2} \leq d < \frac{d_{max}}{R_{original}} + \frac{1}{2} \tag{9}$$

With regard to the rectangular image I4 exemplified in FIG. 4, a concrete example is described. Here, $d_{max}=3$ is set. In this case, since the rectangular image I41 including the lesion P1 has $R_{original}$10/3, the above Expression 7 is satisfied. Thus, the number of divisions in the vertical direction of the rectangular image I41 after resizing is the upper limit value $d_{max}=3$, and the number of divisions in the horizontal direction is d=1 from the above Expression 9. By substituting them in the above Expression 8, the division-number ratio $R_{adjusted}=3$ of the rectangular image I41 after resizing is derived.

In addition, the rectangular image I42 including the lesion P2 has $R_{original}=6/7$, and the above Expression 5 is satisfied. Thus, the division-number ratio of the rectangular image I42 after resizing is $R_{adjusted}=1$. In this manner, since the process differs depending on that the lesion is vertically long, horizontally long, or substantially isotropic, it is possible to appropriately process a lesion area (rectangular image) having any aspect ratio.

The resizing-multiplying-factor calculating unit 14 further searches for the common fraction closest to the reference value of the rectangle aspect ratio of the rectangular image before resizing in such a manner as to minimize the change in the rectangle aspect ratio of the rectangular image including the lesion area to obtain a multiplying-factor for resizing the rectangular image. Specifically, the resizing-multiplying-factor calculating unit 14 calculates, with $R_{adjusted}$, $d_{max}$, $l_x$, and $l_y$, a resizing multiplying-factor $R_{Xresize}$ in the X direction and a resizing multiplying-factor $R_{Yresize}$ in the Y direction of the rectangular image. Here, a method for calculating $R_{Xresize}$ and $R_{Yresize}$ depends on the magnitude of $R_{adjusted}$ and is any one of the following three methods. Here, these three calculation methods correspond to, regarding the rectangular image before resizing, the cases of "$R_{original}$<Th1", "Th1≤$R_{original}$<Th2" and "Th2≤$R_{original}$" as described below. That is, the resizing-multiplying-factor calculating unit 14 calculates the resizing multiplying-factor of the rectangular image by a calculation method which differs depending on the magnitude of the division-number ratio with respect to the predetermined thresholds (Th1 and Th2).

<In the Case of $R_{adjusted}$<1>

This case corresponds to the above case where "the number of divisions in the horizontal direction is sufficiently greater than the number of divisions in the vertical direction", and $R_{adjusted}$ is represented by the above Expression 3. Thus, the resizing-multiplying-factor calculating unit 14 calculates, using the following Expression 10, the resizing multiplying-factor $R_{Xresize}$ for the X Direction and the resizing multiplying-factor $R_{Yresize}$ for the Y Direction. Here, d is a Natural number satisfying the above Expression 4.

[Expression 10]

$$R_{Xresize} = \frac{w_{in} d_{max}}{l_x} \tag{10}$$

$$R_{Yresize} = \frac{h_{in} d}{l_y}$$

<In the Case of $R_{adjusted}$=1>

This case corresponds to the above case where "the number of divisions in the vertical direction is substantially equal to the number of divisions in the horizontal direction", and $R_{adjusted}$ is represented by the above Expression 6. Thus, the resizing-multiplying-factor calculating unit 14 calculates, using the following Expression 11, the resizing multiplying-factor $R_{Xresize}$ for the X direction and the resizing multiplying-factor $R_{Yresize}$ for the Y direction.

[Expression 11]

$$R_{Xresize} = \frac{w_{in} d}{l_x} \tag{11}$$

$$R_{Yresize} = \frac{h_{in} d}{l_y}$$

Here, d is a natural number satisfying the following Expression 12.

[Expression 12]

$$\frac{l_x}{w_{in}} - \frac{1}{2} \leq d < \frac{l_x}{w_{in}} + \frac{1}{2} \tag{12}$$

<In the Case of $R_{adjusted}$>1>

This case corresponds to the above case where "the number of divisions in the vertical direction is sufficiently greater than the number of divisions in the horizontal direction", and $R_{adjusted}$ is represented by Expression 8.

Thus, the resizing-multiplying-factor calculating unit 14 calculates, using the following Expression 13, the resizing multiplying-factor $R_{Xresize}$ for the X direction and the resizing multiplying-factor $R_{Yresize}$ for the Y Direction. Here, d is a Natural number satisfying the above Expression 9.

[Expression 13]

$$R_{Xresize} = \frac{w_{in}d}{l_x} \quad (13)$$
$$R_{Yresize} = \frac{h_{in}d_{max}}{l_y}$$

In the concrete example of the rectangular image I4 described with reference to FIG. 4, the rectangular image I41 including the lesion P1 has $R_{adjusted}=3$. Thus, the resizing multiplying-factor for the X direction and the resizing multiplying-factor for the Y direction of the rectangular image I41 are derived using Expression 13 as $R_{Xresize}=4/3$ and $R_{Yresize}=6/5$, respectively.

In addition, the rectangular image I42 including the lesion P2 has $R_{adjusted}=1$. Thus, the resizing multiplying-factor for the X direction and the resizing multiplying-factor for the Y direction of the rectangular image I42 are derived using Expression 11 and Expression 12 as $R_{Xresize}=8/7$ and $R_{Yresize}=4/3$, respectively.

The image resizing unit 15 resizes the rectangular image with the resizing multiplying-factor calculated in A4 (step A5). Specifically, the image resizing unit 15 multiplies the cropped rectangular image by $R_{Xresize}$ in the X direction and by $R_{Yresize}$ in the Y direction. That is, the size of the rectangular image after resizing in the X direction is $l_x \times R_{Xresize}$, and the size in the Y direction is $l_y \times R_{Yresize}$. The image resizing unit 15 outputs the rectangular image after resizing to the lesion image dividing unit 16.

Figure 5:
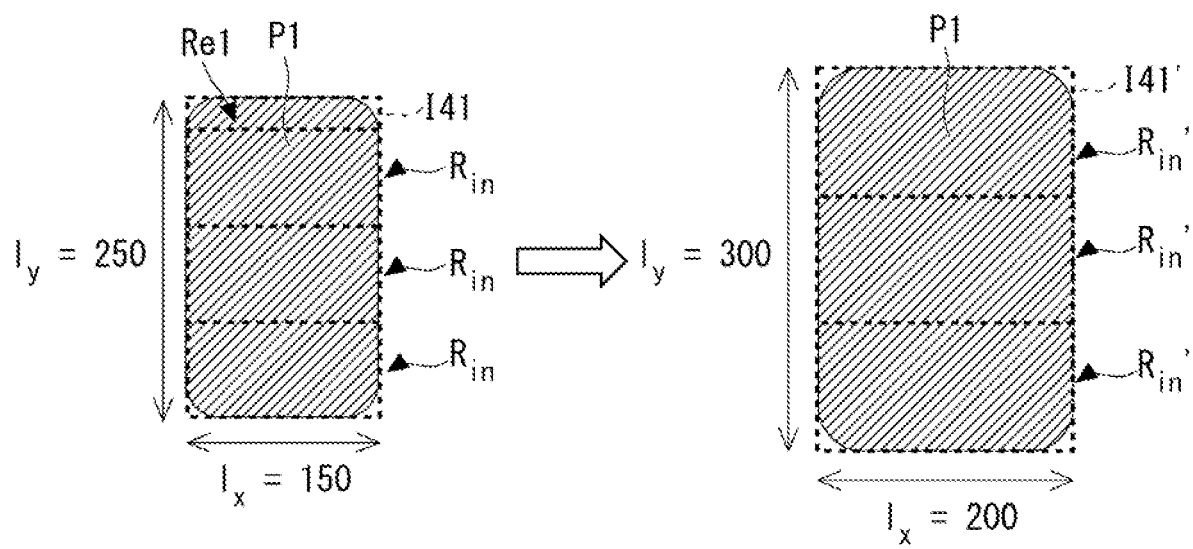
FIG. 5 is a diagram for explaining a process of an image resizing unit according to the first example embodiment.
Figure 6:
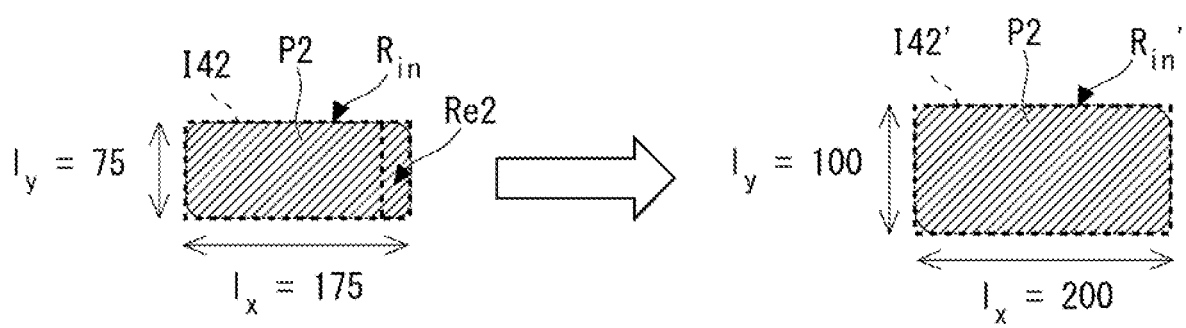
FIG. 6 is a diagram for explaining the process the image resizing unit according to the first example embodiment.

FIGS. 5 and 6 are diagrams for explaining a process of the image resizing unit 15 according to the first example embodiment. FIG. 5 exemplifies that the rectangular image I41 including the lesion P1 exemplified in FIG. 4 is being resized. FIG. 6 exemplifies that the rectangular image I42 including the lesion P2 exemplified in FIG. 4 is being resized.

As exemplified in FIG. 5, the rectangular image I41 having the size of 250×150 pixels is resized to a rectangular image I41' having the size of 300×200 pixels. Accordingly, the rectangular image I41' includes three rectangles $R_{in}'$ (100×200 pixels) each having the size of the input image I3 and no residual portion. In other words, the rectangular image I41 before resizing includes the residual portion Re1, but the rectangular image I41' after resizing does not include any residual portion except for the rectangles $R_{in}'$ each having the image aspect ratio.

In addition, as exemplified in FIG. 6, the rectangular image I42 having the size of 75×175 pixels is resized to a rectangular image I42' having the size of 100×200 pixels. Accordingly, the rectangular image I42' includes one rectangle $R_{in}'$ (100×200 pixel) having the size of the input image I3 and no residual portion. In other words, the rectangular image I42 before resizing includes the residual portion Re2, but the rectangular image I42' after resizing does not include any residual portion except for the rectangle $R_{in}'$ having the image aspect ratio.

The lesion image dividing unit 16 divides the resized rectangular image by the input image size (step A6). Specifically, the lesion image dividing unit 16 divides the resized rectangular image in such a manner that the size of each divided rectangular image is to be the input image size, that is, $h_{in} \times w_{in}$. In the example shown in FIG. 5, the rectangular image after resizing is divided into three images. In the example shown in FIG. 6, the rectangular image after resizing is divided into one image (in this case, the rectangular image after resizing is not substantially divided). Then, the lesion image dividing unit 16 outputs a data string for the obtained images to the lesion identifying device 20.

The lesion identifying device 20 identifies the lesion in each divided rectangular image and calculates a score (step A7). Specifically, the lesion identifying device 20 calculates, as a numeral from 0 to 1, a score indicating how likely each rectangular image divided by the $h_{in} \times w_{in}$ size is to be a certain lesion (for example, a lesion A) among a plurality of lesions to be identified. At this time, the score is 0 if there is no lesion-likeness, and the score approaches to 1 As the lesion-likeness increases. Note that, by using, for example, machine learning or the like, it is possible to calculate the score of a lesion-likeness of the input rectangular image.

The lesion identifying device 20 integrates the score of each divided rectangular image and outputs a diagnostic result to the display device 30 (step A8). Specifically, the lesion identifying device 20 integrates the lesion-likeness score of each rectangular image and calculates the score of the target medical image as a whole. The integration method may be a method using, for example, an arithmetic mean, a maximum value, or the like. The lesion identifying device 20 further compares the integrated score of the target medical image as a whole with a threshold between 0 and 1 predetermined by the user and outputs the diagnostic result based on the comparison result. For example, when the integrated score is equal to or greater than the threshold, the diagnostic result indicating that the lesion in the target medical image is highly likely to be the identified lesion (for example, the lesion A) is output.

Then, the display device 30 displays the diagnostic result (step A9). Accordingly, it is possible for the user to check the diagnosis result of the lesion in the medical image.

[Effects]

Figure 7:
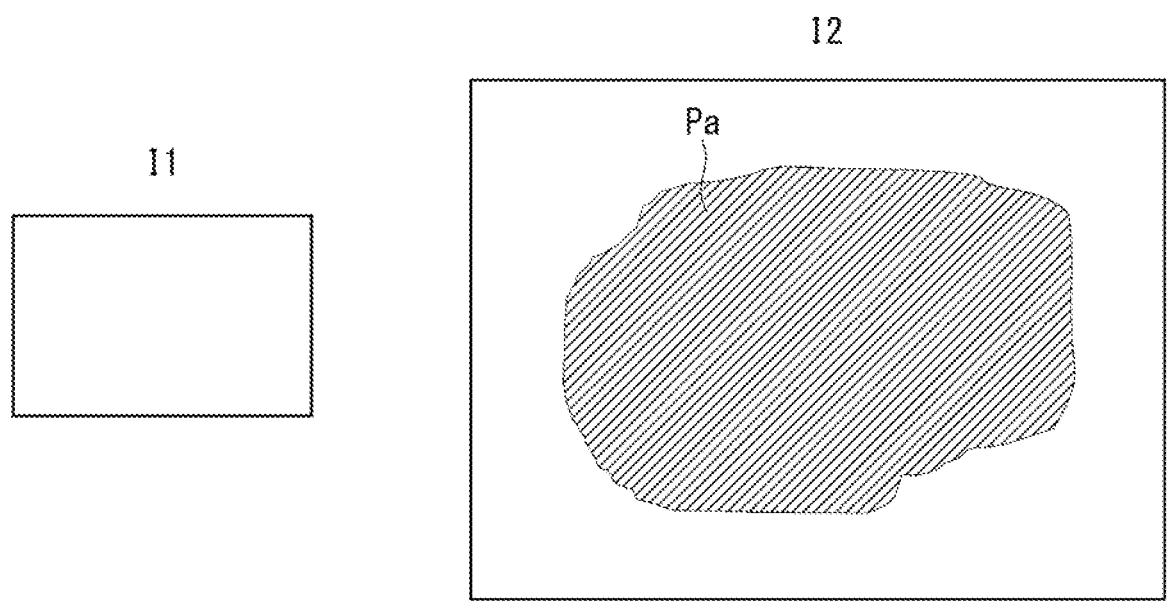
FIG. 7 is a diagram for explaining an effect of the medical image diagnostic system according to the present example embodiment.
Figure 8:
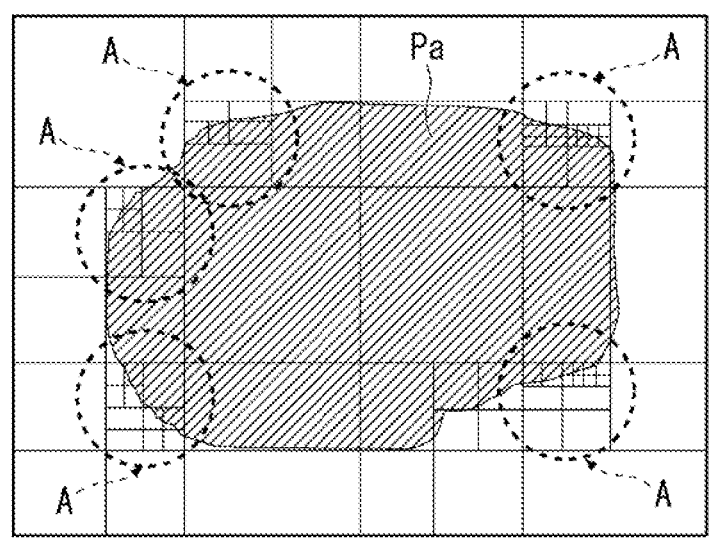
FIG. 8 is a diagram for explaining the effect of the medical image diagnostic system according to the present example embodiment.
Figure 9:
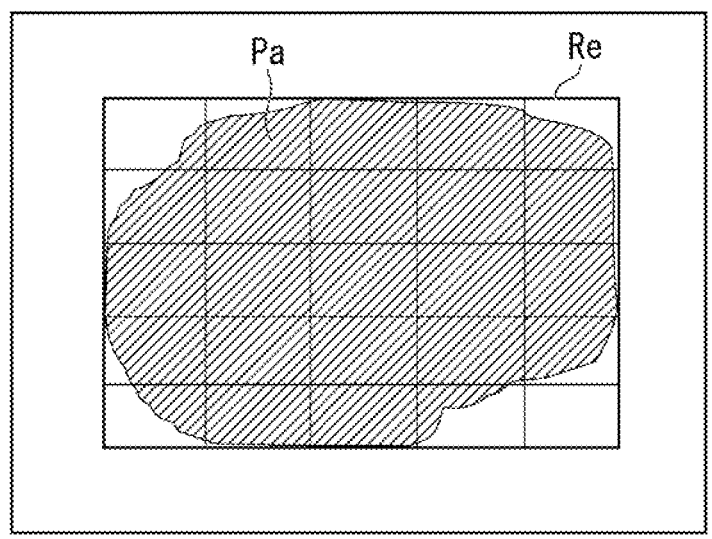
FIG. 9 is a diagram for explaining the effect of the medical image diagnostic system according to the present example embodiment.

Next, effects of the medical image diagnostic system 100 according to the present example embodiment are described with reference to FIGS. 7 to 9. FIGS. 7 to 9 are diagrams for explaining the effects of the medical image diagnostic system 100 according to the present example embodiment. FIG. 7 exemplifies an input image I1 and a medical image I2. FIG. 8 shows an example when a medical image is processed by the method according to the comparable example in Patent Literature 1. FIG. 9 shows an example when a medical image is processed by the method according to the first example embodiment.

The medical image I2 exemplified in FIG. 7 includes an imaged lesion Pa having a complicated shape. When the medical image I2 is divided to be input to a lesion identifying device by the method according to the comparable example, some areas (indicated by arrows A) are exceedingly subdivided as exemplified in FIG. 8. In this case, a subdivided area needs to be enlarged to have the size of the input image I1 in order to be input to the lesion identifying device. For this reason, the resolution of the lesion Pa becomes rough, and the lesion identifying device cannot accurately identify the lesion Pa. This can cause deterioration in the accuracy of diagnosis.

In contrast, when the medical image I2 is divided to be input to a lesion identifying device by the method according to the first example embodiment, the rectangular image encircled by the rectangle Re circumscribing the lesion Pa can be equally divided into areas each having the size matching the size of the input image I1 as exemplified in FIG. 9. In the example shown in FIG. 9, the medical image I2 is equally divided into 5×5=25 areas each having the size of the input image I1. Thus, it is possible for the method according to the first example embodiment to prevent generation of the exceedingly subdivided areas as shown in the comparable example exemplified in FIG. 8. Accordingly, it is possible for the method according to the first example embodiment to prevent deterioration in the accuracy of identification of the lesion Pa by the lesion identifying device. Thus, it is possible to prevent deterioration in the diagnosis accuracy.

In addition, as described above, in the method according to the first example embodiment, the resizing multiplying-factor is calculated to adjust the number of divisions in the vertical direction and the number of divisions in the horizontal direction in order to match the input image size. That is, the lesion area dividing device 10 according to the first example embodiment is configured to calculate the division-number ratio based on the image aspect ratio and the rectangle aspect ratio and to calculate, based on the division-number ratio, the resizing multiplying-factor for each of the vertical direction and the horizontal direction of the rectangular image. Then, the lesion area dividing device 10 according to the first example embodiment is configured to resize the rectangular image with this resizing multiplying-factor and to divide the rectangular image after resizing in such a manner that the size of each divided image matches the size of the input image. Accordingly, it is possible to prevent the rectangle aspect ratio of the rectangular image from excessively greatly changing from that of the rectangular image before resizing to that after resizing and to match the size of each divided image with the size of the input image.

The lesion area in a medical image is varied in shape and is vertically long or horizontally long. In this case, if, for example, a vertically-long lesion area is greatly enlarged in the horizontal direction to match the aspect ratio of the input image, the shape of the lesion area is greatly changed. Thus, the diagnosis accuracy can be deteriorated. In contrast, the method according to the first example embodiment is configured as above, and it is possible to prevent deterioration in the accuracy of identification of the lesion Pa by the lesion identifying device. Thus, it is possible to prevent deterioration in the diagnosis accuracy.

In addition, the lesion area dividing device 10 according to the first example embodiment is configured to calculate the resizing multiplying-factor of the rectangular image by a calculation method which differs depending on the magnitude of the division-number ratio (Expression 1) with respect to the predetermined thresholds (Th1 and Th2). Accordingly, the process changes depending on whether the longitudinal direction of the lesion area is the vertical direction or the horizontal direction, and it is possible to appropriately process a lesion area having any rectangle aspect ratio.

In addition, the lesion area dividing device 10 according to the first example embodiment calculates the division-number ratio (Expression 3, Expression 6, or Expression 8) of the rectangular image after resizing by a calculation method which differs depending on the magnitude of the division-number ratio (Expression 1) with respect to the predetermined thresholds (Th1 and Th2). Then, the lesion area dividing device 10 according to the first example embodiment is configured to calculate the resizing multiplying-factor of the rectangular image in such a manner as to be the division-number ratio after resizing when the rectangular image is divided. Accordingly, the rectangular image is resized in such a manner that the division-number ratio of the rectangular image after resizing is close to the division-number ratio before resizing. Thus, it is possible to prevent the rectangle aspect ratio from excessively greatly changing before and after resizing.

In addition, the lesion area dividing device 10 according to the first example embodiment is configured to calculate the division-number ratio after resizing in such a manner that the number of divisions in the vertical direction and the number of divisions in the horizontal direction of the rectangular image after resizing do not exceed the predetermined upper limit value $d_{max}$ of the number of divisions. Accordingly, it is possible to prevent the rectangular image from being excessively finely divided.

In addition, the resizing-multiplying-factor calculating unit 14 according to the first example embodiment sets the number of divisions in the horizontal direction of the rectangular image after resizing as the upper limit value $d_{max}$ when the division-number ratio calculated by the division-number-ratio calculating unit 13 is less than the threshold Th1. Then, the resizing-multiplying-factor calculating unit 14 according to the first example embodiment calculates, based on the upper limit value, the resizing multiplying-factor for the horizontal direction of the rectangular image after resizing. Accordingly, it is possible to appropriately calculate the resizing multiplying-factor if the lesion area is horizontally long. Thus, it is not necessary to classify the shape of the lesion area into a vertically long shape or a horizontally long shape.

In addition, the resizing-multiplying-factor calculating unit 14 according to the first example embodiment sets the number of divisions in the vertical direction of the rectangular image after resizing as the upper limit value $d_{max}$ when the division-number ratio calculated by the division-number-ratio calculating unit 13 is equal to or greater than the threshold Th2. Then, the resizing-multiplying-factor calculating unit 14 according to the first example embodiment calculates, based on the upper limit value, the resizing multiplying-factor for the vertical direction of the rectangular image after resizing. Accordingly, it is possible to appropriately calculate the resizing multiplying-factor if the lesion area is vertically long. Thus, it is not necessary to classify the shape of the lesion area into a vertically long shape or a horizontally long shape.

In addition, the resizing-multiplying-factor calculating unit 14 according to the first example embodiment sets the number of divisions in the horizontal direction and the number of divisions in the vertical direction of the rectangular image after resizing to be equal to each other when the division-number ratio calculated by the division-number-ratio calculating unit 13 is equal to or greater than the threshold Th1 and is less than the threshold Th2. Accordingly, it is possible to appropriately calculate the resizing multiplying-factor if the shape of the lesion area is substantially isotropic in the vertical direction and in the horizontal direction. Thus, it is not necessary to classify the shape of the lesion area into a vertically long shape or a horizontally long shape.

(Hardware Configuration)

Figure 10:
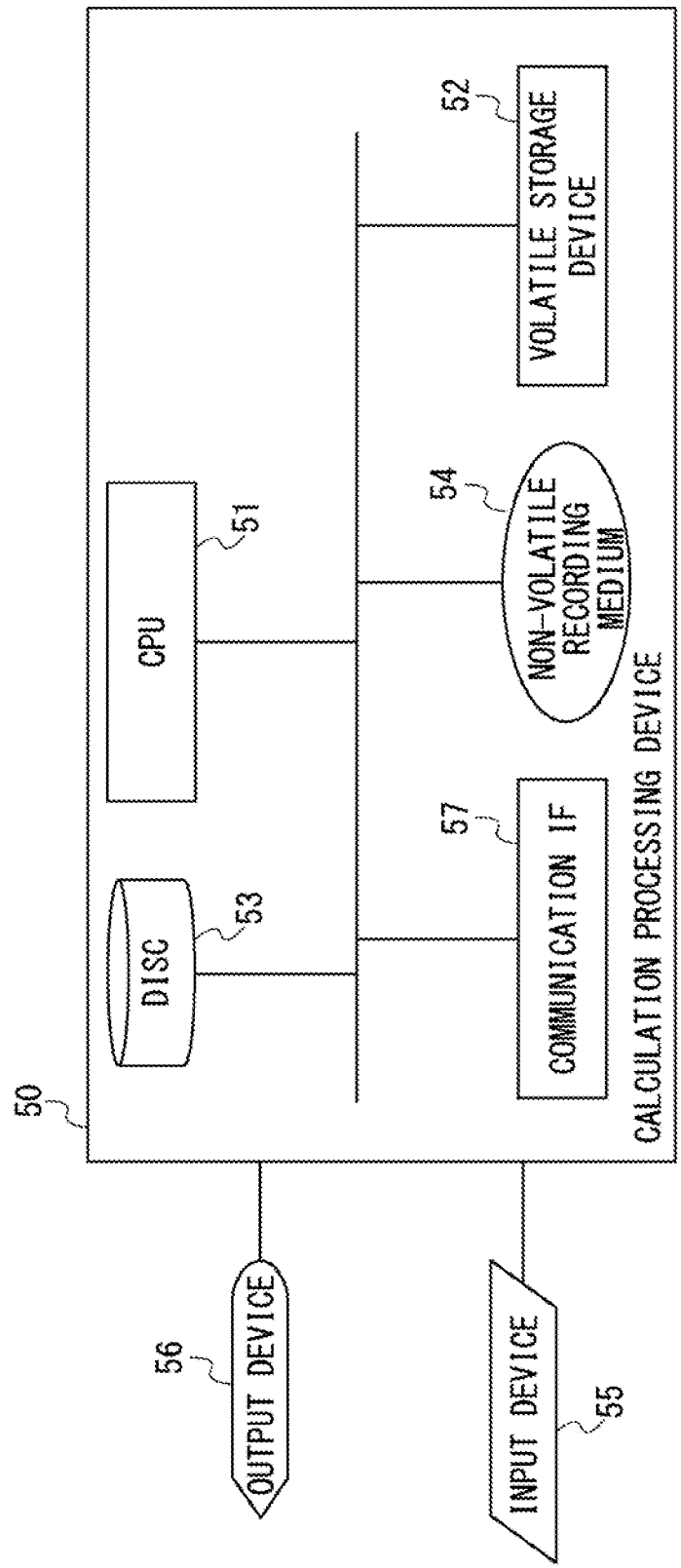
FIG. 10 is a block diagram schematically showing a hardware configuration example of a calculation processing device applicable to the medical image diagnostic system according to the first example embodiment.

FIG. 10 is a block diagram schematically showing a hardware configuration example of a calculation processing device 50 applicable to the medical image diagnostic system 100 according to the first example embodiment. The calculation processing device 50 is capable of implementing the lesion area dividing device 10, the lesion identifying device 20, and the display device 30 shown in FIG. 2.

The calculation processing device 50 includes a CPU 51, a volatile storage device 52, a disc 53, a non-volatile recording medium 54, and a communication interface (IF) 57. Thus, each device or the medical image diagnostic system 100 can be said to include the CPU 51, the volatile storage device 52, the disc 53, the non-volatile recording medium 54, and the communication IF 57. The calculation processing device 50 may be connectable to an input device 55 and an output device 56. The calculation processing device 50 may further include the input device 55 and the output device 56. In addition, the calculation processing device 50 can transmit and receive information to and from other calculation processing devices and communication devices via the communication IF 57.

The non-volatile recording medium 54 is, for example, a computer-readable compact disc or a digital versatile disc. Alternatively, the non-volatile recording medium 54 may be a USB memory, a solid state drive, or the like. The non-volatile recording medium 54 enables a program to be held and carried without being supplied with power. Note that, the non-volatile recording medium 54 is not limited to the above media. In addition, the program may be supplied via the communication IF 57 and a communication network instead of the non-volatile recording medium 54.

The volatile storage device 52 is readable by a computer and temporarily store data. The volatile storage device 52 is a memory, such as a dynamic random access memory (DRAM) or a static random access memory (SRAM), or the like.

That is, the CPU 51 copies a software program (computer program; simply referred to as a "program" in the following) stored in the disc 53 to the volatile storage device 52 to execute the program and performs arithmetic processing. The CPU 51 reads data necessary for executing the program from the volatile storage device 52. The CPU 51 displays the output result on the output device 56 if display is needed. The CPU 51 acquires the program from the input device 55 if the program is input externally. The CPU 51 interprets and executes the program (FIG. 3 and the like) corresponding to the function (process) of each constituent element shown in FIG. 1 or 2. The CPU 51 performs the processes described in the above example embodiment. In other words, the function of each constituent element shown in FIG. 1 or 2 can be implemented by the CPU 51 executing the program stored in the disc 53 or the volatile storage device 52. In addition, the processes shown in FIG. 3 can be implemented by the CPU 51 executing the program stored in the disc 53 or the volatile storage device 52.

That is, it can be considered that the present example embodiment is also achievable by such a program. In addition, it can be considered that the present example embodiment is achievable by a computer-readable nonvolatile recording medium storing such a program.

(Modification)

Note that, the present invention is not limited to the above example embodiment and can be modified without departing from the scope thereof. For example, the order of the processes (steps) in the above flowchart can be appropriately changed. In addition, one or more processes of a plurality of processes (steps) may be omitted. For example, the processes A7 to A9 in the flowchart in FIG. 3 may be omitted. That is, the present example embodiment is achievable by only the lesion area dividing method (A1 to A6 in FIG. 3) performed by the lesion area dividing device 10.

In addition, as described above, the program can be stored using various non-transitory computer-readable media and supplied to a computer. The non-transitory computer-readable media include various tangible storage media. The non-transitory computer-readable media include, as examples, a magnetic recording medium (for example, a flexible disc, a magnetic tape, or a hard disk drive), a magneto-optical recording medium (for example, a magneto-optical disc), a CD-read only memory (ROM), a CD-R, a CD-R/W, and a semiconductor memory (for example, a mask ROM, a programmable ROM (PROM), an erasable PROM (EPROM), a flash ROM, or a random access memory (RAM)). In addition, the program may be supplied to a computer by various transitory computer-readable media. The transitory computer-readable media include, as examples, an electrical signal, an optical signal, and an electromagnetic wave. The transitory computer-readable media can supply the program to a computer via a wired communication channel, such as an electric wire and an optical fiber, or a wireless communication channel.

A part or all of the above example embodiment may be described as the following Supplementary notes but is not limited to the following.

(Supplementary Note 1)

A lesion area dividing device comprising:

a rectangle creating means for creating a rectangle circumscribing a lesion area in a medical image;

a division-number-ratio calculating means for calculating, based on an image aspect ratio of an input image to be input to a device configured to identify a lesion and on a rectangle aspect ratio between a length in a vertical direction and a length in a horizontal direction of the rectangle, a division-number ratio of the number of divisions in a vertical direction to the number of divisions in a horizontal direction when the lesion area is divided;

a multiplying-factor calculating means for calculating, based on the division-number ratio, a resizing multiplying-factor for each of a vertical direction and a horizontal direction of a rectangular image encircled by the rectangle and including the lesion area;

a resizing means for resizing the rectangular image with the resizing multiplying-factor; and a dividing means for dividing the resized rectangular image into one or more images in such a manner that a size of each divided image matches a size of the input image.

(Supplementary Note 2)

The lesion area dividing device according to Supplementary note 1, wherein the multiplying-factor calculating means calculates the resizing multiplying-factor of the rectangular image by a calculation method which differs depending on a magnitude of the division-number ratio with respect to a predetermined threshold.

(Supplementary Note 3)

The lesion area dividing device according to Supplementary note 2, wherein the multiplying-factor calculating means calculates the division-number ratio of the rectangular image after resizing by a calculation method which differs depending on a magnitude of the division-number ratio with respect to a predetermined threshold to calculate the resizing multiplying-factor of the rectangular image in such a manner as to be the division-number ratio after the resizing when the dividing means performs the dividing.

(Supplementary Note 4)

The lesion area dividing device according to Supplementary note 3, wherein the multiplying-factor calculating means calculates the division-number ratio after the resizing in such a manner that the number of divisions in the vertical direction and the number of divisions in the horizontal direction of the rectangular image after the resizing do not exceed a predetermined upper limit value of a number of divisions.

(Supplementary Note 5)

The lesion area dividing device according to Supplementary note 4, wherein the multiplying-factor calculating means sets, when the division-number ratio calculated by the division-number-ratio calculating means is less than a first threshold less than 1 predetermined depending on the upper limit value, the number of divisions in the horizontal direction of the rectangular image after the resizing as the upper limit value to calculate, based on the upper limit value, the resizing multiplying-factor for the horizontal direction of the rectangular image after the resizing.

(Supplementary Note 6)

The lesion area dividing device according to Supplementary note 4, wherein the multiplying-factor calculating means sets, when the division-number ratio calculated by the division-number-ratio calculating means is equal to or greater than a second threshold greater than 1 predetermined depending on the upper limit value, the number of divisions in the vertical direction of the rectangular image after the resizing as the upper limit value to calculate, based on the upper limit value, the resizing multiplying-factor for the vertical direction of the rectangular image after the resizing.

(Supplementary Note 7)

The lesion area dividing device according to Supplementary note 4, wherein the multiplying-factor calculating means sets, when the division-number ratio calculated by the division-number-ratio calculating means is equal to or greater than a first threshold less than 1 predetermined depending on the upper limit value and is less than a second threshold greater than 1 predetermined depending on the upper limit value, the number of divisions in the horizontal direction and the number of divisions in the vertical direction of the rectangular image after the resizing to be equal to each other.

(Supplementary Note 8)

A medical image diagnostic system comprising:
a lesion area dividing device configured to divide a lesion area in a medical image; and
a lesion identifying device configured to identify a lesion using the divided lesion area, wherein
the lesion area dividing device comprises:
  a rectangle creating means for creating a rectangle circumscribing the lesion area;
  a division-number-ratio calculating means for calculating, based on an image aspect ratio of an input image to be input to the lesion identifying device and on a rectangle aspect ratio between a length in a vertical direction and a length in a horizontal direction of the rectangle, a division-number ratio of the number of divisions in a vertical direction to the number of divisions in a horizontal direction when the lesion area is divided;
  a multiplying-factor calculating means for calculating, based on the division-number ratio, a resizing multiplying-factor for each of a vertical direction and a horizontal direction of a rectangular image encircled by the rectangle and including the lesion area;
  a resizing means for resizing the rectangular image with the resizing multiplying-factor; and
  a dividing means for dividing the resized rectangular image into one or more images in such a manner that a size of each divided image matches a size of the input image, and
the lesion identifying device is configured to identify a lesion using each divided image.

(Supplementary Note 9)

The medical image diagnostic system according to Supplementary note 8, wherein the multiplying-factor calculating means calculates the resizing multiplying-factor of the rectangular image by a calculation method which differs depending on a magnitude of the division-number ratio with respect to a predetermined threshold.

(Supplementary Note 10)

The medical image diagnostic system according to Supplementary note 9, wherein the multiplying-factor calculating means calculates the division-number ratio of the rectangular image after resizing by a calculation method which differs depending on a magnitude of the division-number ratio with respect to a predetermined threshold to calculate the resizing multiplying-factor of the rectangular image in such a manner as to be the division-number ratio after the resizing when the dividing means performs the dividing.

(Supplementary Note 11)

The medical image diagnostic system according to Supplementary note 10, wherein the multiplying-factor calculating means calculates the division-number ratio after the resizing in such a manner that the number of divisions in the vertical direction and the number of divisions in the horizontal direction of the rectangular image after the resizing do not exceed a predetermined upper limit value of a number of divisions.

(Supplementary Note 12)

The medical image diagnostic system according to Supplementary note 11, wherein the multiplying-factor calculating means sets, when the division-number ratio calculated by the division-number-ratio calculating means is less than a first threshold less than 1 predetermined depending on the upper limit value, the number of divisions in the horizontal direction of the rectangular image after the resizing as the upper limit value to calculate, based on the upper limit value, the resizing multiplying-factor for the horizontal direction of the rectangular image after the resizing.

(Supplementary Note 13)

The medical image diagnostic system according to Supplementary note 11, wherein the multiplying-factor calculating means sets, when the division-number ratio calculated by the division-number-ratio calculating means is equal to or greater than a second threshold greater than 1 predetermined depending on the upper limit value, the number of divisions in the vertical direction of the rectangular image after the resizing as the upper limit value to calculate, based on the upper limit value, the resizing multiplying-factor for the vertical direction of the rectangular image after the resizing.

(Supplementary Note 14)

The medical image diagnostic system according to Supplementary note 11, wherein the multiplying-factor calculating means sets, when the division-number ratio calculated by the division-number-ratio calculating means is equal to or greater than a first threshold less than 1 predetermined depending on the upper limit value and is less than a second threshold greater than 1 predetermined depending on the upper limit value, the number of divisions in the horizontal direction and the number of divisions in the vertical direction of the rectangular image after the resizing to be equal to each other.

(Supplementary Note 15)

A lesion area dividing method comprising:
creating a rectangle circumscribing a lesion area in a medical image;
calculating, based on an image aspect ratio of an input image to be input to a device configured to identify a lesion and on a rectangle aspect ratio between a length in a vertical direction and a length in a horizontal direction of the rectangle, a division-number ratio of the number of divisions in a vertical direction to the number of divisions in a horizontal direction when the lesion area is divided;
calculating, based on the division-number ratio, a resizing multiplying-factor for each of a vertical direction and a horizontal direction of a rectangular image encircled by the rectangle and including the lesion area;
resizing the rectangular image with the resizing multiplying-factor; and
dividing the resized rectangular image into one or more images in such a manner that a size of each divided image matches a size of the input image.

(Supplementary Note 16)

The lesion area dividing method according to Supplementary note 15, further comprising calculating the resizing multiplying-factor of the rectangular image by a calculation method which differs depending on a magnitude of the division-number ratio with respect to a predetermined threshold.

(Supplementary Note 17)

The lesion area dividing method according to Supplementary note 16, further comprising calculating the division-number ratio of the rectangular image after resizing by a calculation method which differs depending on a magnitude of the division-number ratio with respect to a predetermined threshold to calculate the resizing multiplying-factor of the rectangular image in such a manner as to be the division-number ratio after the resizing when the dividing is performed.

(Supplementary Note 18)

The lesion area dividing method according to Supplementary note 17, further comprising calculating the division-number ratio after the resizing in such a manner that the number of divisions in the vertical direction and the number of divisions in the horizontal direction of the rectangular image after the resizing do not exceed a predetermined upper limit value of a number of divisions.

(Supplementary Note 19)

The lesion area dividing method according to Supplementary note 18, further comprising setting, when the calculated division-number ratio is less than a first threshold less than 1 predetermined depending on the upper limit value, the number of divisions in the horizontal direction of the rectangular image after the resizing as the upper limit value to calculate, based on the upper limit value, the resizing multiplying-factor for the horizontal direction of the rectangular image after the resizing.

(Supplementary Note 20)

The lesion area dividing method according to Supplementary note 18, further comprising setting, when the calculated division-number ratio is equal to or greater than a second threshold greater than 1 predetermined depending on the upper limit value, the number of divisions in the vertical direction of the rectangular image after the resizing as the upper limit value to calculate, based on the upper limit value, the resizing multiplying-factor for the vertical direction of the rectangular image after the resizing.

(Supplementary Note 21)

The lesion area dividing method according to Supplementary note 18, further comprising setting, when the calculated division-number ratio is equal to or greater than a first threshold less than 1 predetermined depending on the upper limit value and is less than a second threshold greater than 1 predetermined depending on the upper limit value, the number of divisions in the horizontal direction and the number of divisions in the vertical direction of the rectangular image after the resizing to be equal to each other.

(Supplementary Note 22)

A non-transitory computer-readable medium storing a program causing a computer to execute:
a step of creating a rectangle circumscribing a lesion area in a medical image;
a step of calculating, based on an image aspect ratio of an input image to be input to a device configured to identify a lesion and on a rectangle aspect ratio between a length in a vertical direction and a length in a horizontal direction of the rectangle, a division-number ratio of the number of divisions in a vertical direction to the number of divisions in a horizontal direction when the lesion area is divided;
a step of calculating, based on the division-number ratio, a resizing multiplying-factor for each of a vertical direction and a horizontal direction of a rectangular image encircled by the rectangle and including the lesion area;
a step of resizing the rectangular image with the resizing multiplying-factor; and
a step of dividing the resized rectangular image into one or more images in such a manner that a size of each divided image matches a size of the input image.

The present invention has been described above with reference to the example embodiment but is not limited by the above. Various modifications that can be understood by those skilled in the art can be made to the configurations and the details of the present invention without departing from the scope of the invention.

This application is based upon and claims the benefit of priority from Japanese Patent Application No. 2019-024745, filed on Feb. 14, 2019, the disclosure of which is incorporated herein in its entirety by reference.

REFERENCE SIGNS LIST

1 Lesion area dividing device
2 Rectangle creating unit
3 Division-number-ratio calculating unit
4 Multiplying-factor calculating unit
5 Resizing unit
6 Dividing unit
10 Lesion area dividing device
11 Lesion area specifying unit
12 Circumscribed-rectangle creating unit
13 Division-number-ratio calculating unit
14 Resizing-multiplying-factor calculating unit
15 Image resizing unit
16 Lesion image dividing unit
20 Lesion identifying device
30 Display device
50 Calculation processing device
100 Medical image diagnostic system

What is claimed is:

1. A lesion area dividing device comprising:
hardware, including a processor and memory;
a rectangle creating unit implemented at least by the hardware and configured to create a rectangle circumscribing a lesion area in a medical image;
a division-number-ratio calculating unit implemented at least by the hardware and configured to calculate a ratio of an image aspect ratio of an input image to be input to a device configured to identify a lesion to a rectangle aspect ratio between a length in a vertical direction and a length in a horizontal direction of the rectangle, as a division-number ratio of a number of divisions in a vertical direction to a number of divisions in a horizontal direction when a rectangular image encircled by the rectangle and including the lesion area is divided;
a multiplying-factor calculating unit implemented at least by the hardware and configured to calculate, based on the division-number ratio, a resizing multiplying-factor for each of the vertical direction and the horizontal direction of the rectangular image;
a resizing unit implemented at least by the hardware and configured to resize the rectangular image with the resizing multiplying-factor; and
a dividing unit implemented at least by the hardware and configured to divide the resized rectangular image into one or more images in such a manner that a size in the vertical direction of each divided image matches a size in the vertical direction of the input image and a size in the horizontal direction of each divided image matches a size in the horizontal direction of the input image,
wherein the multiplying-factor calculating unit, by a calculation method which differs depending on a magnitude of the division-number ratio with respect to a threshold determined based on a predetermined upper limit value of a number of divisions,
calculates a number of divisions in the short-side direction based on the upper limit value and the division-number ratio,
calculates, based on the upper limit value and the number of divisions in the short-side direction, the division-number ratio of the rectangular image after resizing in such a manner that the number of divisions in the vertical direction and the number of divisions in the horizontal direction of the rectangular image after the resizing do not exceed the upper limit value, and
calculates, based on a comparison of the division-number ratio after resizing with 1, sizes in the vertical direction and in the horizontal direction of the rectangular image and sizes in the vertical direction and in the horizontal direction of the input image, the resizing multiplying-factor for resizing the rectangular image in the vertical direction and in the horizontal direction in such manner that the resized rectangular image does not include any residual portion other than a rectangle having the size of the input image.

2. The lesion area dividing device according to claim 1, wherein the multiplying-factor calculating unit sets, when the division-number ratio calculated by the division-number-ratio calculating unit is less than a first threshold that is less than 1 and that is predetermined depending on the upper limit value, the number of divisions in the horizontal direction of the rectangular image after the resizing as the upper limit value to calculate, based on the upper limit value, the resizing multiplying-factor for the horizontal direction of the rectangular image after the resizing.

3. The lesion area dividing device according to claim 1, wherein the multiplying-factor calculating unit sets, when the division-number ratio calculated by the division-number-ratio calculating unit is equal to or greater than a second threshold that is greater than 1 and that is predetermined depending on the upper limit value, the number of divisions in the vertical direction of the rectangular image after the resizing as the upper limit value to calculate, based on the upper limit value, the resizing multiplying-factor for the vertical direction of the rectangular image after the resizing.

4. The lesion area dividing device according to claim 1, wherein the multiplying-factor calculating unit sets, when the division-number ratio calculated by the division-number-ratio calculating unit is equal to or greater than a first threshold that is less than 1 and that is predetermined depending on the upper limit value and is less than a second threshold that is greater than 1 and that is predetermined depending on the upper limit value, the number of divisions in the horizontal direction and the number of divisions in the vertical direction of the rectangular image after the resizing to be equal to each other.

5. A medical image diagnostic system comprising:
a lesion area dividing device configured to divide a lesion area in a medical image; and
a lesion identifying device configured to identify a lesion using the divided lesion area,
wherein the lesion area dividing device comprises:
hardware, including a processor and memory;
a rectangle creating unit implemented at least by the hardware and configured to create a rectangle circumscribing the lesion area;
a division-number-ratio calculating unit implemented at least by the hardware and configured to calculate a ratio of an image aspect ratio of an input image to be input to a device configured to identify a lesion to a rectangle aspect ratio between a length in a vertical direction and a length in a horizontal direction of the rectangle, as a division-number ratio of a number of divisions in a vertical direction to a number of divisions in a horizontal direction when a rectangular image encircled by the rectangle and including the lesion area is divided;
a multiplying-factor calculating unit implemented at least by the hardware and configured to calculate, based on the division-number ratio, a resizing multiplying-factor for each of the vertical direction and the horizontal direction of the rectangular image;
a resizing unit implemented at least by the hardware and configured to resize the rectangular image with the resizing multiplying-factor; and
a dividing unit implemented at least by the hardware and configured to divide the resized rectangular image into one or more images in such a manner that a size in the vertical direction of each divided image matches a size in the vertical direction of the input image and a size in the horizontal direction of each divided image matches a size in the horizontal direction of the input image,
wherein the multiplying-factor calculating unit, by a calculation method which differs depending on a magnitude of the division-number ratio with respect to a threshold determined based on a predetermined upper limit value of a number of divisions, calculates a number of divisions in the short-side direction based on the upper limit value and the division-number ratio, calculates, based on the upper limit value and the number of divisions in the short-side direction, the division-number ratio of the rectangular image after resizing in such a manner that the number of divisions in the vertical direction and the number of divisions in the horizontal direction of the rectangular image after the resizing do not exceed the upper limit value, and calculates, based on a comparison of the division-number ratio after resizing with 1, sizes in the vertical direction and in the horizontal direction of the rectangular image and sizes in the vertical direction and in the horizontal direction of the input image, the resizing multiplying-factor for resizing the rectangular image in the vertical direction and in the horizontal direction in such manner that the resized rectangular image does not include any residual portion other than a rectangle having the size of the input image, and wherein the lesion identifying device is configured to identify a lesion using each divided image.

6. A lesion area dividing method performed by a computer and comprising:

creating a rectangle circumscribing a lesion area in a medical image;

calculating a ratio of an image aspect ratio of an input image to be input to a device configured to identify a lesion to a rectangle aspect ratio between a length in a vertical direction and a length in a horizontal direction of the rectangle, as a division-number ratio of a number of divisions in a vertical direction to a number of divisions in a horizontal direction when a rectangular image encircled by the rectangle and including the lesion area is divided;

calculating, based on the division-number ratio, a resizing multiplying-factor for each of the vertical direction and the horizontal direction of the rectangular image;

resizing the rectangular image with the resizing multiplying-factor; and dividing the resized rectangular image into one or more images in such a manner that a size in the vertical direction of each divided image matches a size in the vertical direction of the input image and a size in the horizontal direction of each divided image matches a size in the horizontal direction of the input image, wherein calculating the resizing multiplying-factor of the rectangular image the multiplying-factor comprises, by a calculation method which differs depending on a magnitude of the division-number ratio with respect to a threshold determined based on a predetermined upper limit value of a number of divisions, calculating a number of divisions in the short-side direction based on the upper limit value and the division-number ratio, calculating, based on the upper limit value and the number of divisions in the short-side direction, the division-number ratio of the rectangular image after resizing in such a manner that the number of divisions in the vertical direction and the number of divisions in the horizontal direction of the rectangular image after the resizing do not exceed the upper limit value, and calculating, based on a comparison of the division-number ratio after resizing with 1, sizes in the vertical direction and in the horizontal direction of the rectangular image and sizes in the vertical direction and in the horizontal direction of the input image, the resizing multiplying-factor for resizing the rectangular image in the vertical direction and in the horizontal direction in such manner that the resized rectangular image does not include any residual portion other than a rectangle having the size of the input image.

7. The lesion area dividing method according to claim 6, further comprising setting, when the calculated division-number ratio is less than a first threshold that is less than 1 and that is predetermined depending on the upper limit value, the number of divisions in the horizontal direction of the rectangular image after the resizing as the upper limit value to calculate, based on the upper limit value, the resizing multiplying-factor for the horizontal direction of the rectangular image after the resizing.

8. The lesion area dividing method according to claim 6, further comprising setting, when the calculated division-number ratio is equal to or greater than a second threshold that is greater than 1 and that is predetermined depending on the upper limit value, the number of divisions in the vertical direction of the rectangular image after the resizing as the upper limit value to calculate, based on the upper limit value, the resizing multiplying-factor for the vertical direction of the rectangular image after the resizing.

9. The lesion area dividing method according to claim 6, further comprising setting, when the calculated division-number ratio is equal to or greater than a first threshold that is less than 1 and that is predetermined depending on the upper limit value and is less than a second threshold that is greater than 1 and that is predetermined depending on the upper limit value, the number of divisions in the horizontal direction and the number of divisions in the vertical direction of the rectangular image after the resizing to be equal to each other.

* * * * *